United States Patent
Davidson

(10) Patent No.: US 6,981,946 B2
(45) Date of Patent: Jan. 3, 2006

(54) LOAD SENSING APPLANATION TONOMETER

(75) Inventor: Jeffery C. Davidson, Hamersville, OH (US)

(73) Assignee: J.D. Mueller Company, LLC, Cincinnati, OH (US)

( * ) Notice: Subject to any disclaimer, the term of this patent is extended or adjusted under 35 U.S.C. 154(b) by 305 days.

(21) Appl. No.: 10/417,825

(22) Filed: Apr. 17, 2003

(65) Prior Publication Data
US 2004/0210123 A1  Oct. 21, 2004

(51) Int. Cl.
A61B 3/16 (2006.01)

(52) U.S. Cl. .................. 600/405; 600/398
(58) Field of Classification Search ........... 600/398, 600/399, 403–406, 561, 587
See application file for complete search history.

(56) References Cited

U.S. PATENT DOCUMENTS

| | | | |
|---|---|---|---|
| 3,070,997 A | | 1/1963 | Papritz et al. |
| 3,470,736 A | * | 10/1969 | Bartfay ............ 600/405 |
| 3,934,462 A | | 1/1976 | Rende |
| 3,992,926 A | | 11/1976 | Berryhill |
| 4,213,464 A | | 7/1980 | Katz et al. |
| 4,523,597 A | | 6/1985 | Sawa et al. |
| 4,759,370 A | | 7/1988 | Kozin et al. |
| 4,951,671 A | | 8/1990 | Coan |
| 4,987,899 A | | 1/1991 | Brown |
| 5,190,042 A | | 3/1993 | Hock |
| 5,203,331 A | | 4/1993 | Draeger |
| 5,363,155 A | | 11/1994 | Urinowski et al. |
| 5,671,737 A | | 9/1997 | Harosi |
| 6,234,966 B1 | | 5/2001 | Miwa |
| 6,394,968 B1 | | 5/2002 | Wallace |
| 6,413,214 B1 | | 7/2002 | Yang |
| 6,440,070 B2 | | 8/2002 | Israel |
| 6,447,449 B1 | | 9/2002 | Fleischman et al. |
| 6,623,429 B2 | * | 9/2003 | Percival et al. ......... 600/399 |
| 6,776,756 B2 | * | 8/2004 | Feldon et al. ......... 600/405 |

FOREIGN PATENT DOCUMENTS

JP  2003-111732  * 4/2003

* cited by examiner

Primary Examiner—Charles Marmor
(74) Attorney, Agent, or Firm—Wood, Herron & Evans, LLP

(57) ABSTRACT

An improved applanation tonometer for measuring the intraocular pressure of an eye is configured for use with a conventional slit lamp. This applanation tonometer has a force sensor that senses the force applied by an applanation probe to flatten the cornea of the eye, while the cornea is viewed through the probe using the slit lamp. The force sensor generates a signal that corresponds to the applanation force and transmits the signal to a display and/or a data storage device.

15 Claims, 7 Drawing Sheets

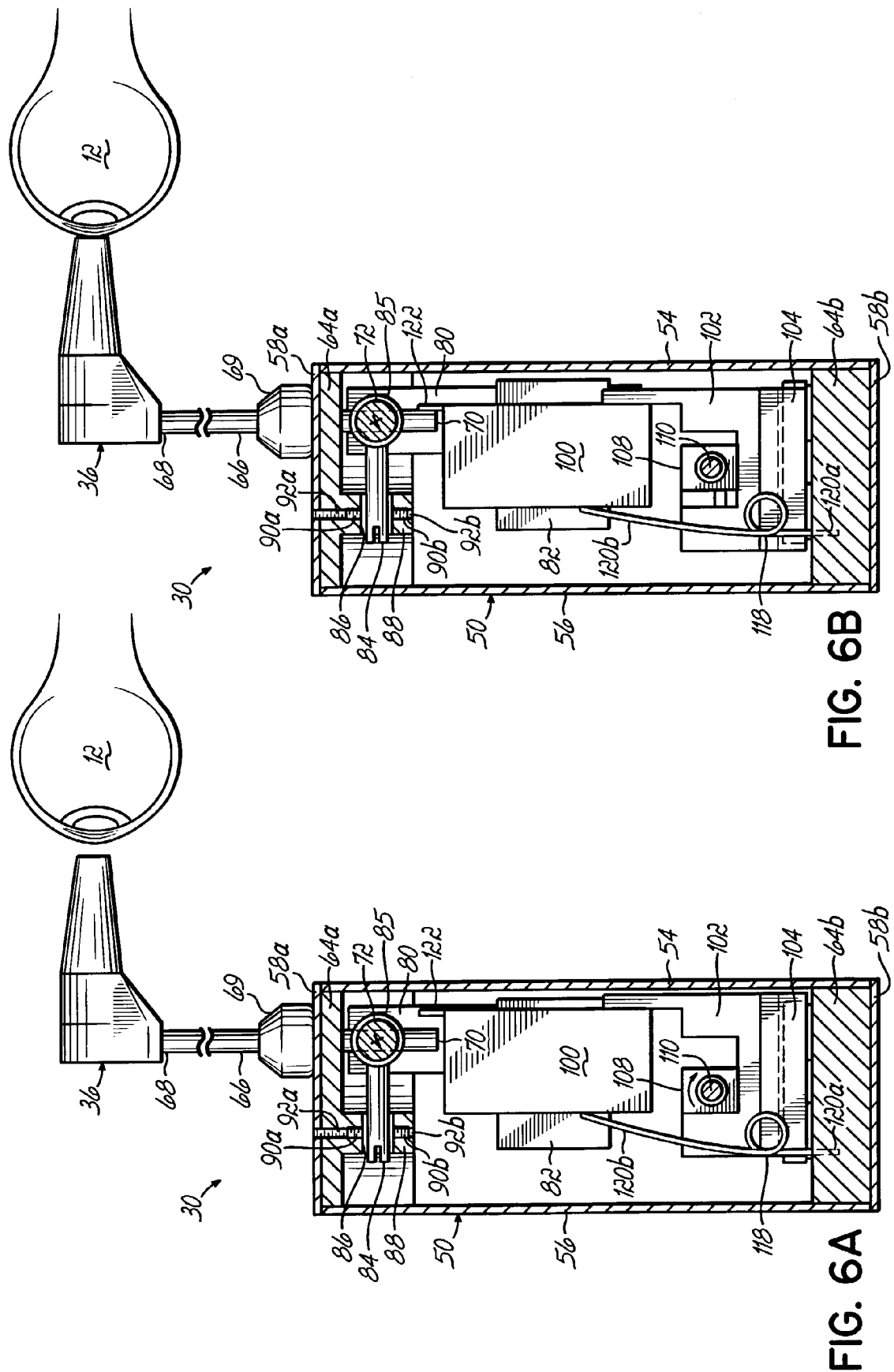

LOAD SENSING APPLANATION TONOMETER

FIELD OF THE INVENTION

The present invention pertains to medical diagnostic systems, and more particularly to an improved applanation tonometer with greater reliability in measuring the intraocular pressure of an eye.

BACKGROUND OF THE INVENTION

Tonometers are known in the art and are widely used to facilitate indirect measurement of the intraocular pressure of a person's eye. The ability to obtain measurements of intraocular pressure has proved important for detecting diseases, such as glaucoma, or other ailments of the eye.

Various types of tonometers have been developed and may be classified, generally, as non-contact tonometers, indentation tonometers and applanation tonometers. Non-contact tonometers generally utilize a puff of air applied to the cornea of an eye in conjunction with shining a light beam onto the eye. As the cornea becomes flattened by the puff of air, the light intensity reflected from the cornea of the eye varies and is detected by an optical device. Non-contact type tonometers are generally considered by medical professionals to be less accurate than contact-type tonometers and thus are primarily used for initial screening purposes.

While non-contact type tonometers do not actually touch the eye, indentation tonometers and applanation tonometers include members that are actually brought into physical contact with the cornea of an eye to depress a portion of the cornea while obtaining a measurement of force. An indentation tonometer utilizes a weighted plunger to apply a known force to the cornea while measuring the deformation produced. An applanation tonometer measures the force required to flatten a predetermined area of the cornea. By far the most widely used mechanical tonometer is the Goldmann applanation tonometer, described in U.S. Pat. No. 3,070,997. Using the Goldmann applanation tonometer, the cornea of an eye being tested is flattened with a probe having a 3.06 mm diameter flat area. Once the cornea has been flattened to the 3.06 mm diameter, the force required to flatten the cornea is measured and used to calculate the internal pressure of the eye.

While the Goldmann applanation tonometer is widely used and familiar to practitioners, it also suffers several drawbacks. For example, the Goldmann-type tonometer is a complex mechanical system comprising internal weights, springs and bearings which must be periodically calibrated to ensure accurate measurements of intraocular eye pressure. This drawback is heightened by the fact that there are relatively few persons who have the resources and technical capability for performing these periodic calibrations. Furthermore, the Goldmann applanation tonometer is susceptible to error due to improper balancing or level orientation of the tonometer with respect to the microscope and is sensitive to interference from electromagnetic fields. Accordingly, there is thus a need for an applanation tonometer which overcomes drawbacks of the prior art such as those described above.

SUMMARY OF THE INVENTION

The present invention overcomes these drawbacks by incorporating into an applanation tonometer a force sensor that is configured to sense the force applied by the probe to the cornea of the patient's eye, and to generate a signal corresponding to the sensed force. This inventive applanation tonometer has an applanation probe containing a prism system that, when viewed through a microscope assembly, generates a visual indication when a desired area of the cornea of a patient's eye has been flattened by the probe. This inventive applanation tonometer can be used with a conventional microscope assembly, such as a biomicroscope slit lamp, in a manner that is familiar to and widely accepted by medical practitioners, to measure the intraocular pressure of a patient's eye. Advantageously, the applanation tonometer of the present invention permits measuring the intraocular pressure of a patient's eye without the need for the complex mechanical calibrations of internal weights, springs, and bearings of prior art devices. Accordingly, the applanation tonometer ensures robust performance without the need for precise balancing and orientation of the device. Furthermore, the need to have specially trained technicians periodically calibrate the system by tediously adjusting these internal components is eliminated. Instead, the force sensor of the present invention may easily be "zeroed-out" by users as required.

The signal generated by the force sensor may be transmitted to a display for indication of the measured intraocular pressure, and/or it may be transmitted to a data storage device configured to receive and store information for individual patients. The display may be part of the applanation tonometer, or it may be a stand alone unit. Alternatively, the display may be configured as a heads-up display that can be viewed by a user through the microscope assembly while applanating the patient's eye with the probe.

In one aspect of the invention, the applanation tonometer includes a housing, and the applanation probe is supported on one end of a support arm movably coupled to the housing. As the probe is brought into contact with the cornea of the patient's eye, the opposite end of the support arm engages the force sensor, whereby force applied to the patient's eye is sensed by the force sensor.

In another aspect of the invention, the support arm is coupled to a rotatable knob configured to move the support arm, and thus the applanation probe supported on the support arm. The probe may be advanced to applanate the cornea by rotating the knob.

In yet another aspect of the invention, an instrument for measuring the intraocular pressure of a patient's eye comprises a stand, a microscope supported on the stand, a slit lamp coupled to the stand, and an applanation tonometer having a prism system and force sensor, as described above.

In another aspect of the invention, a method of measuring intraocular pressure of an eye includes applanating the cornea of the eye, viewing the applanated cornea through a microscope, sensing the force required to applanate the cornea, sending a signal corresponding to the sensed force to an output device, and displaying a value at the output device that corresponds to the sensed force.

The features and objectives of the present invention will become more readily understood from the following Detailed Description and the accompanying drawings.

BRIEF DESCRIPTION OF THE DRAWINGS

FIGS. 6A–6B are cross sectional views of the applanation tonometer of FIG. 5 taken along line 6A—6A and illustrating operation of the applanation tonometer.

DETAILED DESCRIPTION OF THE PREFERRED EMBODIMENT

Figure 1:
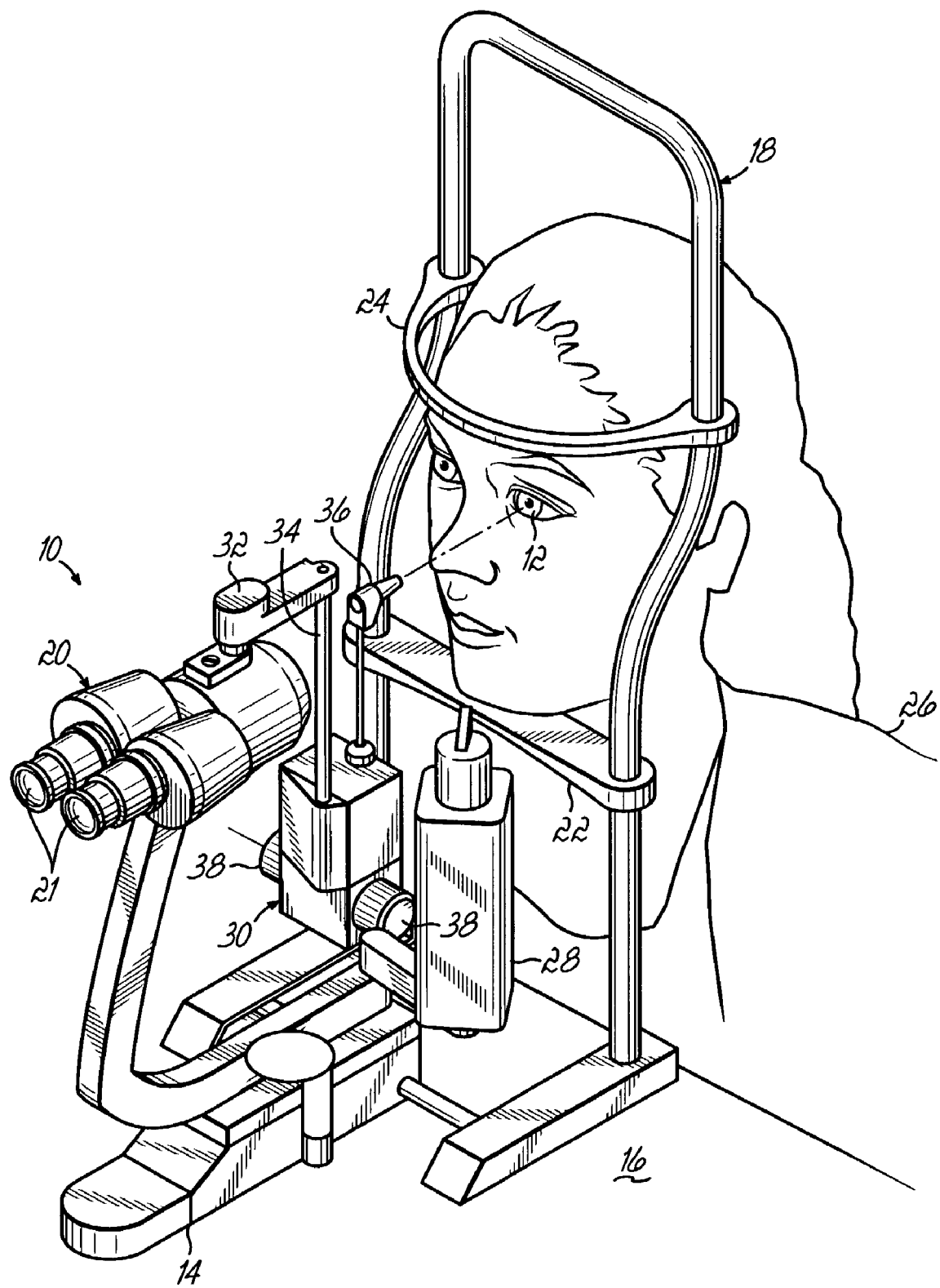
FIG. 1 is a perspective view of a biomicroscope slit lamp including an applanation tonometer in accordance with a preferred embodiment of the invention.

FIG. 1 shows a microscope assembly 10 configured to facilitate the examination of a patient's eye 12, as known in the art. The microscope assembly 10 generally comprises a base 14 which is securely mounted to a table 16, or other secure structure, and a patient support 18 extending upward from the base 14. A microscope 20 is pivotally supported to the base 14 and is shown in FIG. 1 as a biomicroscope, having dual eyepieces 21 for viewing the anatomy of a patient's eye 12. It will be recognized, however, that the microscope 20 may alternatively comprise only a single eyepiece. A chin rest 22 and a head brace 24 are coupled to the patient support 18, in a known manner, whereby a patient 26 may position his or her chin on the chin rest 22 and bring their head forward so that the forehead rests against the head brace 24 to position the patient 26 for observation through the microscope 20. The microscope assembly 10 further includes a slit lamp 28 pivotally mounted to the base 14, whereby the slit lamp 28 may be swung into a position for directing a beam of light into the patient's eye 12, as known in the art.

FIG. 1 shows that the microscope assembly 10 also includes an applanation tonometer 30 of the present invention. The applanation tonometer 30 is pivotally mounted to the microscope assembly 10 by a mount fixture 32 and support arm 34 pivotally coupled to the microscope 20. Alternatively, the exemplary applanation tonometer 30 may be pivotally mounted to an arm (not shown) coupled to the base 14 of the microscope assembly 10.

Figure 2:
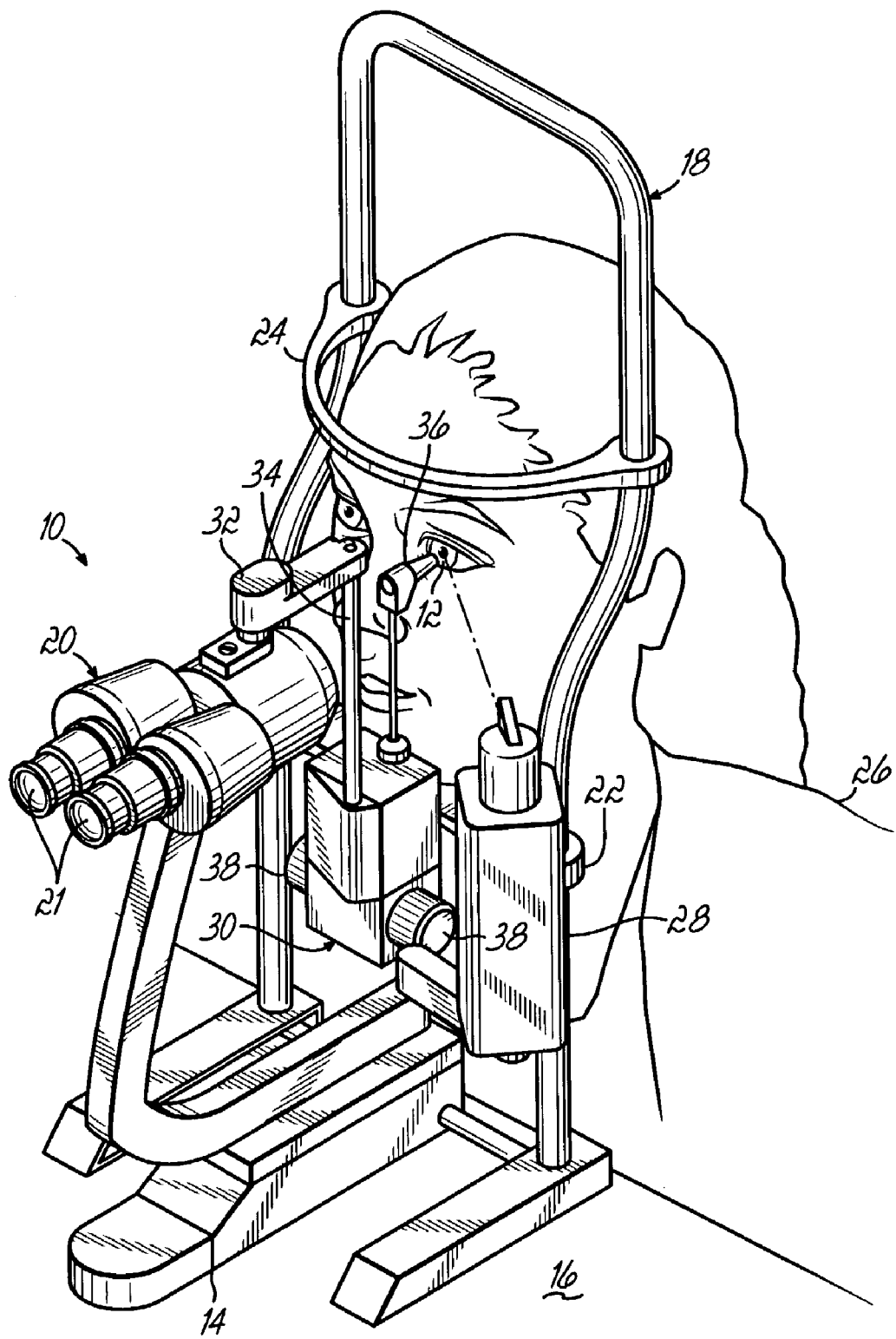
FIG. 2 illustrates the tonometer of FIG. 1 during applanation of a subject's eye.
Figure 3:
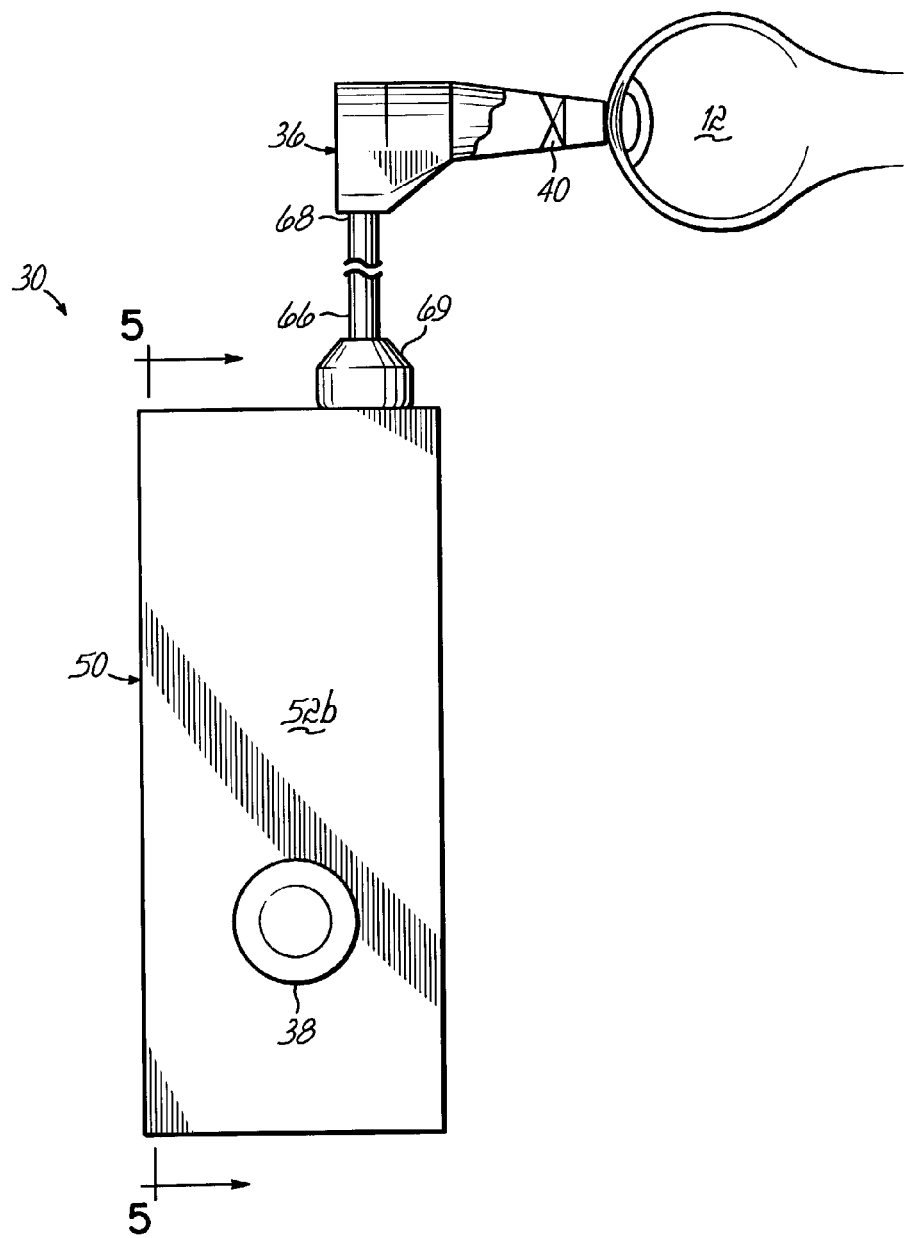
FIG. 3 is a side view of the exemplary applanation tonometer of FIG. 1.

With the patient 26 in position, the applanation tonometer 30 and microscope 20 may be moved forward such that a probe 36 of the applanation tonometer 30 may be brought into contact with the cornea of the patient's eye 12, as depicted in FIG. 2. FIG. 2 further illustrates use of the slit lamp 28 to direct a beam of light into the patient's eye 12 while applanating the cornea with the probe 36 of the tonometer 30, all while viewing the applanated cornea through the microscope 20. Just prior to contact with the cornea, the positions of the microscope 20 and tonometer 30 are firmly secured and the probe 36 is advanced to applanate the cornea of the patient's eye 12 using knobs 38 provided on the applanation tonometer 30, as depicted in FIGS. 2 and 3. The probe 36 of the applanation tonometer 30 includes a prism system 40 configured to provide an indication when the cornea of the patient has been applanated to a desired area. This prism system 40 is well known in the art and disclosed in U.S. Pat. No. 3,070,997 to Papritz et al. An exemplary prism system 40 is part no. 0900.2236A, available from Haag-Streit AG, Berne, Switzerland.

Figure 4A:
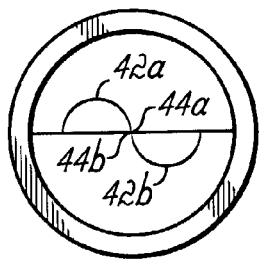
FIGS. 4A–4C are schematic illustrations depicting an applanated cornea viewed through the applanation tonometer of the present invention.
Figure 4B:
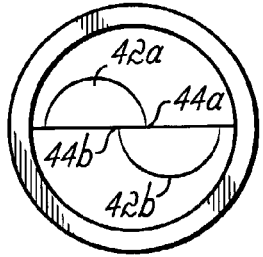
Figure 4C:
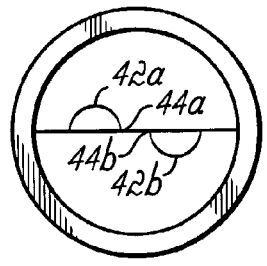

FIGS. 4A–4C illustrate the image created by the prism system 40 while applanating the patient's eye 12, as viewed through the eyepiece 21 of the microscope 20. The prism system 40 creates two semicircular arcs 42a, 42b which translate relative to one another while the probe 36 is advanced to applanate the patient's eye 12. When the probe 36 has applanated the desired area of the cornea, ends 44a, 44b of the respective arcs 42a, 42b coincide to produce a sinusoidal image as depicted in FIG. 4A. When the applanation tonometer 30 has flattened an area of the cornea greater than the desired area, the ends 44a, 44b of the arcs 42a, 42b are offset as depicted in FIG. 4B. Similarly, when the applanation probe 36 flattens an area of the cornea less than the desired area, the arcs 42a, 42b are offset as depicted in FIG. 4C. Accordingly, a user may adjust the position of the probe 36 to obtain the desired applanation area by turning the knob 38 on the tonometer 30 and viewing the applanated cornea through the microscope 20 and probe 36 until the ends 44a, 44b of the respective arcs 42a, 42b coincide as depicted in FIG. 4A. At this point, the applanation probe 36 has flattened the cornea to the desired area for measurement of intraocular pressure.

Figure 8B:
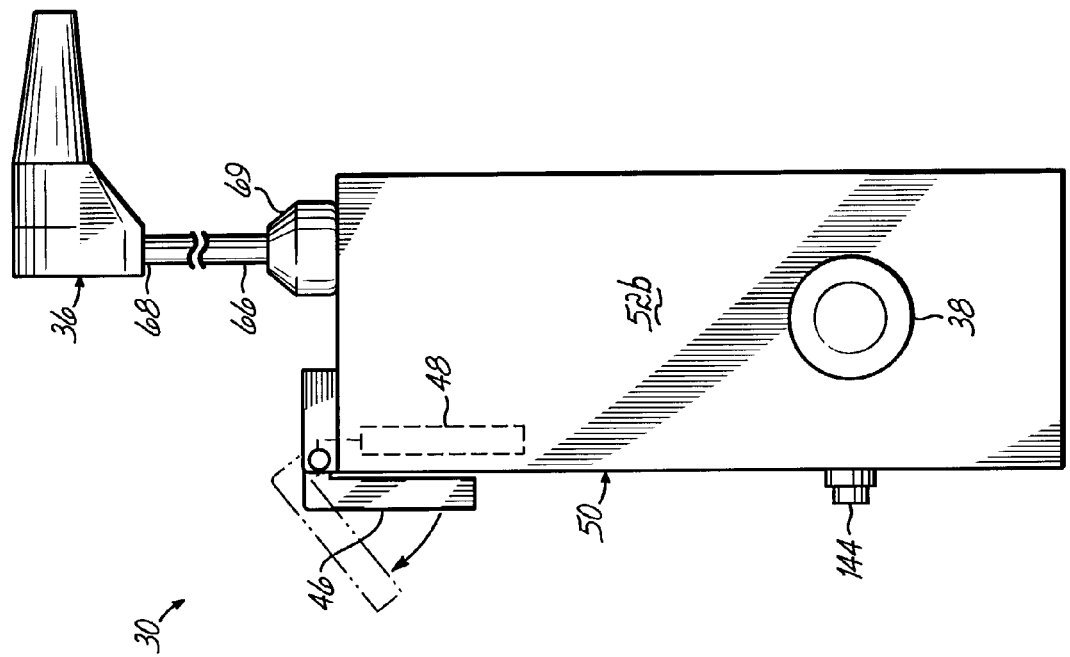
FIGS. 8A–8B are views depicting an exemplary display for the applanation tonometer of FIG. 1.
Figure 8A:
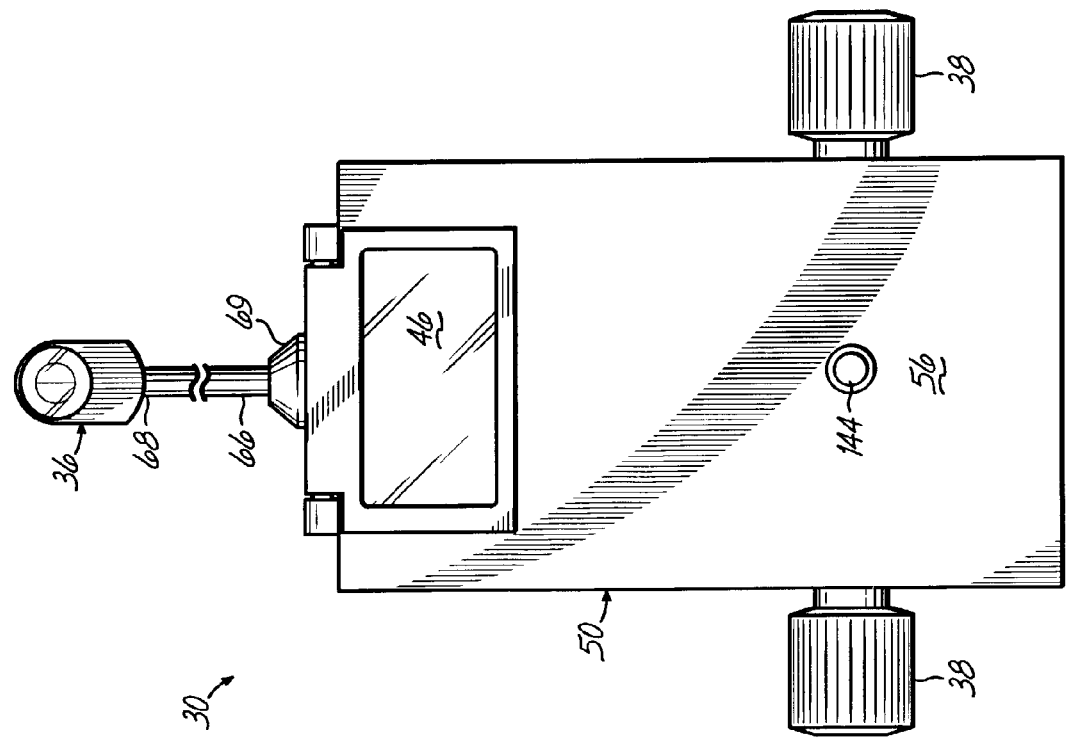

Advantageously, the applanation tonometer 30 is configured to sense the force of the probe 36 against the applanated cornea and to provide to the user a signal representative of the sensed force. In one embodiment, the signal is transmitted to a display 46 that is configured to indicate a value corresponding to the force sensed by the applanation tonometer 30, as depicted in FIGS. 8A–8B. In a preferred embodiment, the display 46 indicates a value representative of the intraocular pressure of the eye 12. The display 46 may be mounted to the microscope assembly 10, such as on the applanation tonometer, for example, as shown in FIGS. 8A–8B, or may be provided on a separate unit. Alternatively, the display 46 may be configured as a heads up display which is viewable through the microscope 20, whereby a user may readily observe the indicated value corresponding to the force of the applanation probe 36 against the cornea, while permitting the user to continue to observe the applanated cornea of the patient 26.

Figure 5:
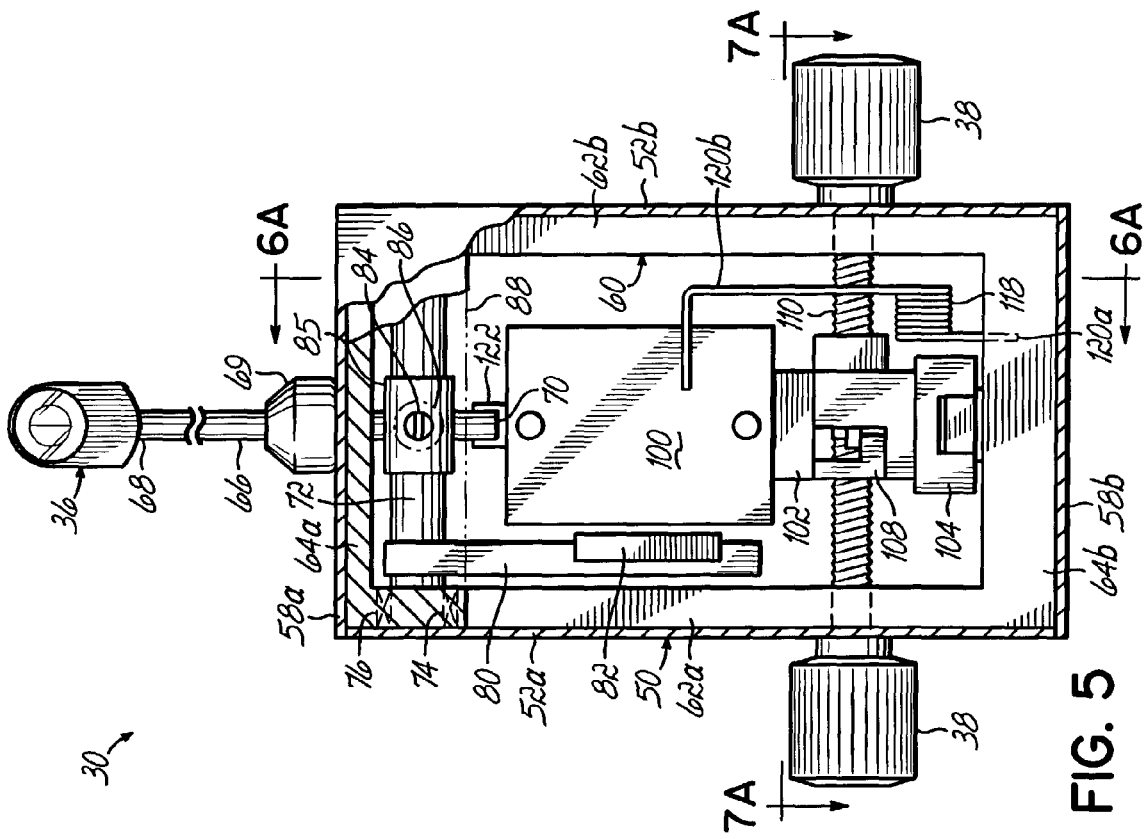
FIG. 5 is a partial cross sectional view of the applanation tonometer of FIG. 3, taken along line 5—5.

FIGS. 5–7 show the construction and operation of the applanation tonometer 30. With particular reference to FIG. 5, the applanation tonometer 30 includes a housing 50 having opposing side walls 52a, 52b, front and rear walls 54, 56, and opposing top and bottom walls 58a, 58b. The side walls 52a, 52b, front and rear walls 54, 56, and top and bottom walls 58a, 58b of the housing 50 are secured to and enclose a frame 60 for supporting the interior components of the applanation tonometer 30. The frame 60 has a generally rectangular shape defined by opposing side plates 62a, 62b and upper and lower plates 64a, 64b. A probe arm 66 extends through a hole formed through the upper plate 64a and top wall 58a of the housing 50 and supports the applanation probe 36 at a distal end 68. A cap 69 disposed on probe arm 66 covers the hole formed through top wall 58a of housing 50. The proximal end 70 of the probe arm 66 is coupled to a horizontal shaft 72 extending between the side plates 62a, 62b of the frame 60. The shaft 72 is coupled at its ends 74 to the side plates 62a, 62b of the frame 60 such that the shaft 72 may be rotated about its longitudinal axis. The ends 74 of the shaft 72 are supported by ball bearings 76 that are press fit into apertures formed in the respective side plates 62a, 62b of the frame 60. In this configuration, the probe arm 66 may pivot about the shaft 72 to permit movement of the applanation probe 36 in a direction substantially transverse to the longitudinal axis of the shaft 72.

A balance arm 80 having a movable balance weight 82 is coupled to the shaft 72 such that the balance weight 82 may be positioned along the balance arm 80 to counteract the moment of force created by the mass of the applanation probe 36 at the distal end 68 of the probe arm 66. The applanation tonometer 30 is configured to limit the motion of the probe 36 to provide controlled applanation of the patient's eye 12. As shown in FIGS. 5, 6A and 6B, a limit adjustment member 84 is coupled to the shaft 72 by a collar 85 and extends generally rearwardly through an aperture 86 formed through a transverse rib 88 extending between the side plates 62a, 62b of the frame 60. Set screws 90a, 90b are installed through tapped holes 92a, 92b in the frame 60 proximate the limit aperture 86, whereby movement of the limit adjustment member 84 in the aperture 86 may be controlled by adjusting the set screws 90a, 90b to provide a desired clearance between the limit adjustment member 84 and the set screws 90a, 90b. In this manner, rotation of shaft 72, and thus movement of applanation probe 36 on probe arm 66, is limited over a desired range.

The applanation tonometer 30 further includes a force sensor 100, such as sensor model No. GSO-100 available from Transducer Technologies, Temecula, Calif., disposed within the housing 50 and configured to sense a force applied to the applanation probe 36. The force sensor 100 is secured to a sensor support 102 slidably coupled to the bottom plate 64b of the frame 60 by a slider mechanism 104, such as Linear Slide No. Y-LMS-156, available from Parker Hannifin Corp., Daedal Division, Irwin, Pa.

Figure 7A:
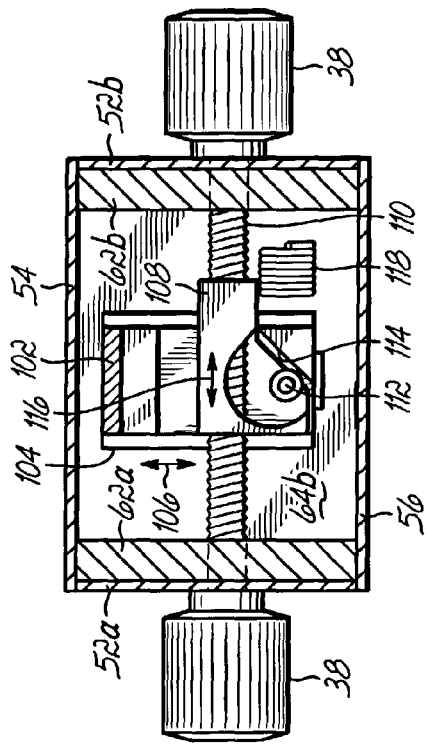
FIGS. 7A–7B are cross sectional views of the applanation tonometer of FIG. 5, taken along line 7A—7A and further illustrating operation of the applanation tonometer.
Figure 7B:
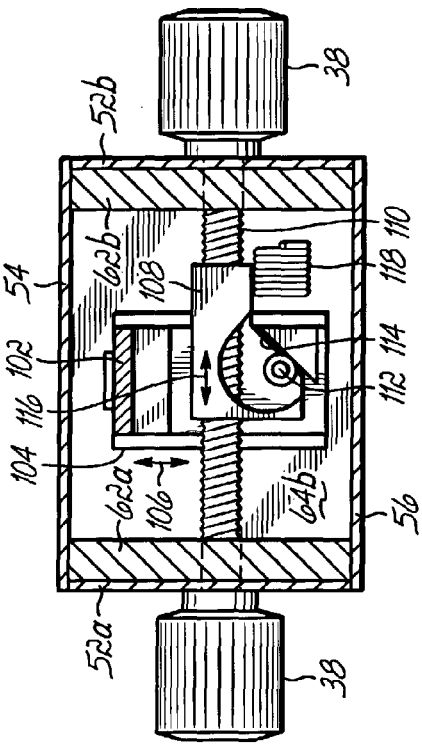

The slider mechanism 104 is configured to constrain the sensor support 102 for linear movement between the front wall 54 and rear wall 56 of the housing. 50, as depicted by arrow 106 in FIGS. 7A and 7B. The sensor support 102 cooperates with a cam 108 that is threadably coupled to a horizontally positioned threaded rod 110 extending between side plates 62a, 62b and coupled to adjustment knobs 38 at its distal ends. Threaded rod 110 rotates in bearings (not shown) installed through apertures in side plates 62a, 62b. The cam 108 has a bearing 112 positioned to contact a follower surface 114 of the sensor support 102 whereby rotation of the knobs 38 causes the cam 108 to move along the threaded rod 110, between side plates 62a, 62b, as indicated by directional arrow 116. A torsion spring 118 is disposed within the housing 50 and has a first spring arm 120a coupled to the lower plate 64b and a second spring arm 120b engaging the force sensor 100 whereby the spring 118 biases the sensor support 102 and force sensor 100 in a direction toward front wall 54. Accordingly, the spring 118 urges the follower surface 114 of the sensor support 102 into engagement with the bearing 112 on the cam 108.

With particular reference to FIGS. 6A–6B and 7A–7B, as knobs 38 are manipulated to cause the cam 108 to move to the left in FIGS. 7A, 7B, as illustrated by arrow 116, bearing 112 on the cam 108 engages the follower surface 114 and causes the sensor support 102 to move in a direction toward the rear wall 56 against the bias force of the spring 118. As shown in FIGS. 6A–6B, as the sensor support 102 moves toward the rear wall 56, an actuating member 122 of the force sensor 100 engages the proximal end 70 of the probe arm 66, thereby causing the probe arm 66 to pivot about the horizontal shaft 72. As the probe arm 66 pivots about horizontal shaft 72, the probe 36 is brought into contact with the cornea of the patient's eye 12 and may be advanced to applanate an area of the patient's eye, limited by the limit adjustment member 84 which also pivots about horizontal shaft 72. While the probe 36 applanates the patient's eye 12, the force required to applanate the patient's eye 12 is transferred through the probe arm 66 and applied to the actuating member 122 of the force sensor 100. The force sensor 100 generates a signal related to the force applied to the cornea of the patient's eye 12. Advantageously, the signal may be transmitted from the force sensor 100 to the display 46 to indicate a value related to the force applied to the cornea of the patient's eye 12. As shown in the figures, the force sensor 100 transmits the signal to the display 46 via a wire. However, it will be recognized that the signal may be transmitted by other structure or devices, such as by radio frequency or infrared transmission paths to the display 46.

FIGS. 8A and 8B show an exemplary display 46 for indicating a value related to the force of the probe 36 that is required to applanate the patient's eye 12 to a desired area. The display 46 is mounted to the housing 50 of the applanation tonometer 30. The display 46 is coupled to an electronic circuit 48 disposed within the housing 50 and depicted by hidden lines in FIG. 8B. The electronic circuit 48 controls the format of the value indicated on the display 46. For example, the circuit 48 may be used to cause the display 46 to indicate the intraocular pressure of the patient's eye in millimeters of mercury, based on the signal received from the force sensor 100. As shown, the display 46 is pivotally coupled to the housing 50, so that it may be adjustably positioned for convenient viewing by a user of the applanation tonometer 30.

Figure 9:
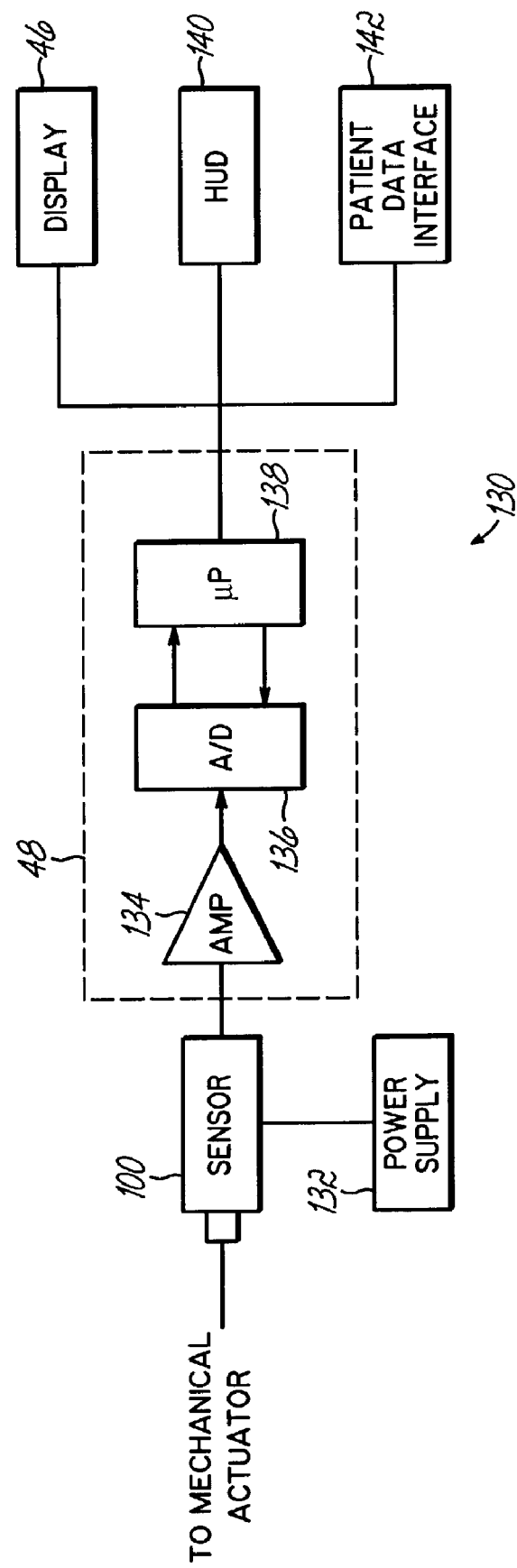
FIG. 9 is an exemplary electrical schematic for an applanation tonometer constructed in accordance with a preferred embodiment of the invention.

FIG. 9 shows an exemplary electrical schematic 130 for the applanation tonometer 30. In FIG. 9, force sensor 100 has a power supply 132, which may be external or may be incorporated internally, as a battery for example. Force sensor 100 communicates with an electric circuit 48, which generally comprises an amplifier 134, an analog-to-digital (A/D) converter 136, and a microprocessor 138. Signals produced by the force sensor 100, in response to engagement of applanation probe 36 with the cornea of a patient's eye 12, are sent to the amplifier 134, A/D converter 136 and microprocessor 138 for conditioning into a signal that can be received and used by various peripheral devices. For example, the conditioned signal from the electronic circuit 48 may be transmitted to the display 46 for indication of intraocular pressure to a user, as described above. Alternatively, the conditioned signal may be transmitted to a separate heads-up display 140 or a patient data interface 142 that is configured to receive and store data from the applanation tonometer that is related to the intraocular pressure for a given patient 26.

Advantageously, the applanation tonometer 30 of the present invention may be used in a manner which is familiar to and well accepted by medical practitioners who are familiar with the well-known Goldmann tonometer. But this invention also provides a convenient display of the force required to applanate a patient's eye 12. Thus, the invention uses the same paradigm that is currently most familiar to medical practitioners, but provides significant advantages over prior conventional devices. More specifically, the applanation tonometer 30 of the present invention overcomes drawbacks of prior art tonometers by eliminating the complex internal mechanisms utilized in those devices and replacing them with a force sensor 100 which provides a digital signal. Accordingly, the applanation tonometer 30 of the present invention is less sensitive to the effects of gravity or electromagnetic fields and can be readily autocalibrated by users, such a by depressing a reset button 144 (FIGS. 8A, 8B), to ensure accurate operation. Moreover, a conventional applanation tonometer may be directly replaced by an applanation tonometer of the present invention, without the need for additional modification of equipment and without the need for practitioners to learn how to use a new type of device.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. An applanation tonometer for measuring the intraocular pressure of an eye using a microscope, comprising:
    a housing configured to be mounted proximate the microscope;
    a support arm having first and second ends, said first end movably coupled to said housing;
    an applanation probe coupled to said second end of said support arm for movement into contact with the cornea of the eye, said probe having a contact surface for applanating the cornea of the eye and a prism assembly cooperating with said contact surface such that the applanated cornea may be viewed through the microscope;
    a force sensor disposed within said housing and engageable with said support arm, whereby force applied to said probe by contact with the applanated cornea is sensed by said sensor through said support arm;
    a display in communication with said sensor and configured to indicate a value corresponding to the force sensed by said force sensor;
    a rotatable knob operatively coupled to said support arm, whereby rotation of the knob causes said support arm to move and thereby move said probe toward or away from the cornea of the eye;
    a slidable base disposed within said housing; and
    a cam coupled between said rotatable knob and said support arm, said cam mounted to said slidable base and configured to convert rotational movement of said knob into translational movement of said base.

2. The applanation tonometer of claim 1, wherein said force sensor is a strain gauge.

3. The applanation tonometer of claim 1, wherein said force sensor is mounted to said slidable base and is moved to engage said support arm by rotation of said knob.

4. The applanation tonometer of claim 1, wherein said support arm is pivotally coupled to said housing.

5. The applanation tonometer of claim 1, wherein said display includes a heads-up display that is viewable through the microscope.

6. The applanation tonometer of claim 1, further comprising a data storage device in communication with said force sensor and configured to store values related to the forces sensed by said force sensor.

7. The applanation tonometer of claim 6, further comprising a wireless signal transmitting device cooperating with said force sensor and configured to communicate with said data storage device, to thereby transmit to said data storage device a signal related to the force sensed by said sensor.

8. The applanation tonometer of claim 1, further comprising a wireless signal transmitting device cooperating with said force sensor and configured to communicate with said display, to thereby transmit to said display a signal corresponding to the force sensed by said force sensor.

9. An applanation tonometer for measuring the intraocular pressure of an eye using a microscope, the applanation tonometer comprising:
    an applanation probe having a contact surface for applanating the cornea of the eye and a prism assembly for indicating a desired applanation area of the eye, said applanation probe cooperating with the microscope to permit the applanated cornea to be viewed through the microscope;
    a force sensor operatively coupled to said probe end configured to generate a signal corresponding to a force applied to the applanated cornea;
    a display in communication with said force sensor and configured to indicate a value corresponding to the force sensed by said force sensor;
    a data storage device in communication with said force sensor and configured to store values related to the forces sensed by said force sensor; and
    a wireless signal transmitting device cooperating with said force sensor and configured to communicate with said data storage device, to thereby transmit to said date storage device a signal related to the force sensed by said force sensor.

10. The applanation tonometer of claim 9, wherein said display includes a heads-up display that is viewable through the microscope.

11. An applanation tonometer for measuring the intraocular pressure of an eye using a microscope, comprising:
    a housing configured to be mounted proximate the microscope;
    a support arm having first and second ends, said first end pivotally coupled to said housing;
    an applanation probe coupled to said second end of said support arm for movement into contact with the cornea of the eye, said probe having a contact surface for applanating the cornea of the eye and a prism assembly cooperating with said contact surface such that the applanated cornea may be viewed through the microscope;
    a force sensor disposed within said housing and engageable with said support arm, whereby force applied to said probe by contact with the applanated cornea is sensed by said sensor through said support arm;
    a display in communication with said sensor and configured to indicate a value corresponding to the force sensed by said force sensor; and
    a weight coupled to said support arm to balance said support arm with respect to said housing.

12. The applanation tonometer of claim 11, further comprising a data storage device in communication with said force sensor and configured to store values related to the forces sensed by said force sensor.

13. The applanation tonometer of claim 12, further comprising a wireless signal transmitting device cooperating with said force sensor and configured to communicate with said data storage device, to thereby transmit to said data storage device a signal related to the force sensed by said sensor.

14. The applanation tonometer of claim 11, further comprising a wireless signal transmitting device cooperating with said force sensor and configured to communicate with said display, to thereby transmit to said display a signal corresponding to the force sensed by said force sensor.

15. An applanation tonometer for measuring the intraocular pressure of an eye using a microscope, comprising:
- a housing configured to be mounted proximate the microscope;
- a support arm having first and second ends, said first end movably coupled to said housing;
- an applanation probe coupled to said second end of said support arm for movement into contact with the cornea of the eye, said probe having a contact surface for applanating the cornea of the eye and a prism assembly cooperating with said contact surface such that the applanated cornea may be viewed through the microscope;
- a force sensor disposed within said housing and engageable with said support arm, whereby force applied to said probe by contact with the applanated cornea is sensed by said sensor through said support arm;
- a display in communication with said sensor and configured to indicate a value corresponding to the force sensed by said force sensor;
- a data storage device in communication with said force sensor and configured to store values related to the forces sensed by said force sensor; and
- a wireless signal transmitting device cooperating with said force sensor and configured to communicate with said data storage device, to thereby transmit to said data storage device a signal related to the force sensed by said force sensor.

* * * * *

UNITED STATES PATENT AND TRADEMARK OFFICE
CERTIFICATE OF CORRECTION

PATENT NO. : 6,981,946 B2 Page 1 of 1
APPLICATION NO. : 10/417825
DATED : January 3, 2006
INVENTOR(S) : Davidson It is certified that error appears in the above-identified patent and that said Letters Patent is hereby corrected as shown below:

Column 6,
Line 65, reads "...such a by depressing a..." and should read -- ...such as by depressing a... --.

Column 8,
Line 15, reads "...coupled to said probe end configured to..." and should read -- ...coupled to said probe and configured to... --.
Line 26, reads "...transmit to said date storage device a..." and should read -- transmit to said data storage device a... --.

Signed and Sealed this

Twentieth Day of June, 2006

JON W. DUDAS
*Director of the United States Patent and Trademark Office*